(12) United States Patent
Shan (10) Patent No.: US 11,642,095 B2
(45) Date of Patent: May 9, 2023

(54) MULTI-AUDIO STETHOSCOPE HEAD

(71) Applicant: WUXI KAISHUN MEDICAL DEVICE MANUFACTURING CO., LTD., Jiangsu (CN)

(72) Inventor: Xijie Shan, Jiangsu (CN)

(73) Assignee: WUXI KAISHUN MEDICAL DEVICE MANUFACTURING CO., LTD., Jiangsu (CN)

( * ) Notice: Subject to any disclaimer, the term of this patent is extended or adjusted under 35 U.S.C. 154(b) by 57 days.

(21) Appl. No.: 17/529,623

(22) Filed: Nov. 18, 2021

(65) Prior Publication Data
US 2022/0087634 A1    Mar. 24, 2022

Related U.S. Application Data

(63) Continuation-in-part of application No. PCT/CN2020/090603, filed on May 15, 2020.

(51) Int. Cl.
| A61B 7/02 | (2006.01) |
| A61B 7/00 | (2006.01) |
| G10K 11/18 | (2006.01) |
| G10K 13/00 | (2006.01) |

(52) U.S. Cl.
CPC .............. *A61B 7/026* (2013.01); *G10K 11/18* (2013.01); *G10K 13/00* (2013.01)

(58) Field of Classification Search
CPC .. A61B 7/026; A61B 7/02; A61B 7/00; A61B 7/04; G10K 11/18; G10K 13/00
See application file for complete search history.

(56) References Cited

U.S. PATENT DOCUMENTS

| 4,167,223 A * | 9/1979 | Liesse ................... | G10K 11/04 381/67 |
| 4,440,258 A * | 4/1984 | Packard .................. | A61B 7/02 181/137 |
| 4,561,447 A * | 12/1985 | Kawamura ............ | A61B 5/021 600/500 |

(Continued)

FOREIGN PATENT DOCUMENTS

| CN | 2862968 Y | 1/2007 |
| CN | 2862969 Y * | 1/2007 |

(Continued)

*Primary Examiner* — Edgardo San Martin
(74) *Attorney, Agent, or Firm* — McDonnell Boehnen Hulbert & Berghoff LLP (57) ABSTRACT

A multi-audio stethoscope head comprising a head body (1) including a sound collecting surface (11), a vibrating diaphragm, and a fastener. The sound collecting surface (11) is provided with a sound guiding hole (16), and the fastener (3) is provided with an axial through hole (33), a fastener sidewall (31) for attaching to the head body (1), and a diaphragm pressing portion (32) for tightly attaching the vibrating diaphragm (2) to the head body (1). The vibrating diaphragm (2) is disposed between the diaphragm pressing portion (32) and the head body (1). Protruding poles (6) protruding toward the vibrating diaphragm (2) is arranged on the sound collecting surface (11) at the radially inner side of the through hole (33), and when the vibrating diaphragm (2) is not subject to external pressure, the vibrating diaphragm (2) is spaced from the protruding poles (6).

15 Claims, 10 Drawing Sheets

(56) References Cited

U.S. PATENT DOCUMENTS

| | | | | |
|---|---|---|---|---|
| 5,796,053 A | * | 8/1998 | Shieh | A61B 7/02 |
| | | | | 181/131 |
| 5,931,792 A | * | 8/1999 | Packard | A61B 7/026 |
| | | | | 600/528 |
| 6,019,186 A | | 2/2000 | Zambrano | |
| 10,398,406 B2 | * | 9/2019 | Keller | A61B 7/02 |
| 2001/0014162 A1 | * | 8/2001 | Orten | A61B 7/04 |
| | | | | 600/528 |
| 2011/0251508 A1 | | 10/2011 | Kassal | |

FOREIGN PATENT DOCUMENTS

| | | | | | |
|---|---|---|---|---|---|
| CN | 101172039 | A | | 5/2008 | |
| CN | 201253219 | Y | * | 6/2009 | |
| CN | 101647712 | A | * | 2/2010 | |
| CN | 201409932 | Y | * | 2/2010 | |
| CN | 201409933 | Y | * | 2/2010 | |
| CN | 201409934 | Y | * | 2/2010 | |
| CN | 101675886 | A | * | 3/2010 | |
| CN | 201847694 | U | * | 6/2011 | |
| CN | 102217950 | A | | 10/2011 | |
| CN | 101647712 | B | * | 11/2011 | |
| CN | 202235434 | U | | 5/2012 | |
| CN | 202263005 | U | | 6/2012 | |
| CN | 105708488 | B | * | 9/2018 | |
| CN | 211633336 | U | * | 10/2020 | A61B 7/026 |
| CN | 111973216 | A | * | 11/2020 | |

\* cited by examiner

MULTI-AUDIO STETHOSCOPE HEAD

CROSS-REFERENCE TO RELATED APPLICATIONS

This application is a continuation-in-part of International Application No. PCT/CN2020/090603, filed May 15, 2020, which claims priority to (i) Chinese Patent Application No. 201910423262.1, filed May 21, 2019, and (ii) Chinese Patent Application No. 201910806127.5, filed Aug. 29, 2019, the contents of each of which are hereby incorporated by reference in their entirety.

TECHNICAL FIELD

The present disclosure relates to a multi audio frequency stethoscope head, and particularly to a stethoscope head which is single-sided and can be used to clearly hear a high-frequency sound without a high-frequency sound collecting ring formed on a sound collecting surface and without changing the size of the sound connecting surface, as well as a method for hearing multiple audio frequencies by using the stethoscope head.

BACKGROUND

An existing stethoscope head includes a head body, a vibrating diaphragm and a fastener for fixing the vibrating diaphragm to the head body.

When the existing stethoscope head is used for hearing multiple audio frequencies by its single side, the size of a sound collecting cavity of the stethoscope head is significantly reduced. However, in the case of hearing multiple audio frequencies via a stethoscope for child by changing the size of the sound collecting cavity thereof, the heard sound is of a significantly reduced volume and thus is unclear, as a result, a high-frequency sound cannot be heard via the stethoscope for child. This is generally because the head body of the stethoscope for child has an outer diameter smaller than that of a head body of a stethoscope for adult and hence has a smaller effective sound collecting cavity, and the sound collected by the stethoscope for child by significantly varying the sound collecting cavity has a decreased volume and cannot be heard clearly.

To facilitate the up and down movements of the vibrating diaphragm in the existing single-sided or double-sided stethoscope in hearing multiple audio frequencies, an elastomer of a laid down-L shaped cross section is coated on an edge of the hard vibrating diaphragm on both upper and lower faces of the vibrating diaphragm. Thus, the whole vibrating diaphragm coated with the elastomer is composed of two different materials, resulting in the following defects in the prior art.

The material of the elastomer is beneficial to the up and down movement of the vibrating diaphragm but is disadvantageous for conduction of sound waves due to the sound absorbing property of the material of the elastomer, and the hard portion with good sound conducting performance (which is typically a sheet of resin fibre or plastics of a 0.2 mm thickness) of the vibrating diaphragm has a reduced diameter due to the adding of the elastomer material given the fixed diameter of the vibrating diaphragm, thus the clarity of the collected sound and the sound conducting property of the vibrating diaphragm is degraded.

Because the whole vibrating diaphragm is composed of two different materials of significantly different hardness, when sound waves are propagating in the vibrating diaphragm, the sound waves are refracted or scattered at an interface between these two different materials because of different hardness and densities and hence different acoustic impedance of the materials, and such refraction or scattering increases an attenuation of the sound waves.

Because the whole vibrating diaphragm is composed of two different materials of significantly different hardness, when sound waves are propagating in the vibrating diaphragm, the sense of depth of the sound collected by the vibrating diaphragm is degraded because the sound waves propagate through two different media (i.e. these two materials) which have different hardness and densities, thus the collected sound is unclear and auscultation quality is lowered.

Therefore, it is a technical problem in the industry to provide a stethoscope head which is applicable to hear multiple audio frequencies (or high-frequency and low-frequency sounds) by merely its single side (i.e. without switching sides of the stethoscope), without changing the original size of the sound collecting surface of the stethoscope head.

SUMMARY

An object of the present disclosure is to provide a multi-audio or dual-audio stethoscope head with an improved sound conducting capability, which can be used to hear organ sounds with improved volume and clarity.

The object of the present disclosure is achieved by the below solution.

A multi-audio stethoscope head includes a head body, a vibrating diaphragm and a fastener, where a sound collecting surface is provided on the head body, a sound guiding hole is provided in the sound collecting surface, and the fastener includes an axial through hole, a fastener sidewall configured for attaching to the head body and a diaphragm pressing portion configured for attaching the vibrating diaphragm to the head body; the vibrating diaphragm is disposed between the diaphragm pressing portion and the head body, and includes an upper surface and a lower surface, where at least one protruding pole is arranged on the sound collecting surface of the head body at an radially inner side of the through hole of the fastener, and a top end of the protruding pole is below the lower surface of the vibrating diaphragm.

On the sound collecting surface of the head body, there may be provided one, two, three, four, five, six or more protruding poles against which the lower surface of the vibrating diaphragm may rest, but the present invention is not limited thereto.

In the above solution, the protruding pole and the head body may be individually made but match with each other or be formed integrally.

In the above solution, when a plurality of the protruding poles are present, the protruding poles are at least partially spaced.

If a number of two or more of the protruding poles are present, the protruding poles may have their bottom ends fixed to the same annular body and thus connected to each other, here, the annular body may be formed integrally with the protruding poles. Alternatively, the protruding poles may have their top ends connected to each other, or have their middle portions connected to each other. No matter whether the protruding poles are completely spaced from each other and fixed or disposed on the sound collecting surface or the protruding poles are partially connected to each other, the sound collecting cavity is not divided into multiple totally disconnected compartments after the protruding poles rest against the vibrating diaphragm.

In the above solution, a support member may be provided on the top end of the protruding pole. For the respective protruding poles, the support members on the protruding poles may be sequentially connected to form a closed shape or be spaced from each other. The shape of the support member is not limited, for example, the support member may have a cross section of a circular shape, a triangle-like shape, an oval shape, a rectangular shape or an irregular shape. The support member on the protruding pole may have an arcuate shape, a curved shape, a linear shape or an irregular shape, but the present disclosure is not limited thereto.

In the above solution, the support member on the protruding pole may be made of an elastic material.

In the above solution, the protruding pole is far away from the outer side of the head body, and the distance from the protruding pole to the sound guiding hole in the sound collecting surface is less than the distance from the protruding pole to the outer side of the head body. For example, a distance from the protruding pole to the center of the sound guiding hole is no more than 50% of the radius of the sound collecting cavity.

In the above solution, the fastener includes an axial through hole, a fastener sidewall configured for attaching to the head body and a diaphragm pressing portion configured for attaching the vibrating diaphragm to the head body. The vibrating diaphragm is disposed between the diaphragm pressing portion and the head body, and includes an upper surface and a lower surface, where a sound enhancing ring is disposed between the vibrating diaphragm and the head body and/or a sound enhancing ring is disposed between the vibrating diaphragm and the diaphragm pressing portion, and the sound enhancing ring is at least partially positioned at a radially outer side of the through hole of the fastener.

In the above solution, the sound enhancing ring is connected or engaged with the upper or lower surface of the vibrating diaphragm to form a portion of contact, which is at least partially positioned between a longitudinal extension plane of a sidewall of the through hole and a longitudinal extension plane of the fastener sidewall or an inner face of the fastener sidewall.

Another object of the present disclosure is to provide a stethoscope head which is used to hear sounds of varied frequencies by its single side, without changing the size of the head body.

The present invention is implemented by a multi-audio stethoscope head, which includes a head body, a vibrating diaphragm and a fastener, at least one protruding pole is arranged on the sound collecting surface of the head body, the vibrating diaphragm is fixed to the head body by the fastener, and the lower surface of the vibrating diaphragm and the sound collecting surface together define a sound collecting cavity. When the vibrating diaphragm is not subjected to an external force, the lower surface of the vibrating diaphragm is spaced from the top end of the protruding pole. That is, the lower surface of the vibrating diaphragm is spaced from the protruding pole in order to hear a sound of a frequency A by the multi-audio stethoscope head, and the lower surface of the vibrating diaphragm rests against the top end of the protruding pole in order to hear a sound of a frequency B by the multi-audio stethoscope head. No matter whether the lower surface of the vibrating diaphragm rests against the protruding pole, the sound collecting cavity is not divided into multiple independent and disconnected compartments, which refers to spaces defined by the vibrating diaphragm and the sound collecting surface.

In the above solution, the protruding pole and the head body may be formed integrally, or may be individually made but match with each other.

There may be provided one, two, three, four, five, six, seven or more protruding poles, but the present invention is not limited thereto In the above solution, the protruding poles are at least partially spaced. The protruding poles may have their top ends connected, or have their middle portions connected, or have their bottom ends connected, so as to ensure that spaces at both sides of the protruding poles are still in communication after the lower surface of the vibrating diaphragm rests against the protruding pole, thereby preventing the sound collecting cavity from being divided into two or more disconnected compartments.

In the above solution, a support member, which may be made of an elastomer, is provided on the top end of the protruding pole. The shape of the support member is not limited, for example, the support member may have a cross section of a circular shape, a triangle-like shape, an oval shape, a rectangular shape or an irregular shape. The support member may have an arcuate shape, a curved shape, a linear shape or an irregular shape, but the present disclosure is not limited thereto.

Still another object of the present invention is to provide a dual-audio stethoscope head which enhances the sound conducting property of the existing hard vibrating diaphragm and facilitates the up and down movements of the vibrating diaphragm, so that sounds can be heard clearly during auscultation.

The particular implementation is as follows. A multi-audio stethoscope head includes a head body, a vibrating diaphragm and a fastener; the fastener includes a through hole and a diaphragm pressing portion configured for pressing the vibrating diaphragm; the vibrating diaphragm includes an upper surface and a lower surface and is arranged between the fastener and the head body by using the fastener; where a sound enhancing ring is disposed between the lower surface of the vibrating diaphragm and the head body and/or a sound enhancing ring is disposed between the upper surface of the vibrating diaphragm and the fastener, and a portion of contact between the sound enhancing ring and the vibrating diaphragm is positioned right below the diaphragm pressing portion. Here, the sound enhancing ring is made of elastic material and the vibrating diaphragm may be a hard diaphragm sheet with a uniform thickness or with nonuniform thickness. The sound enhancing ring is useful for enhancing soundwaves and facilitates downward deformation or movement of the vibrating diaphragm when the surface of the vibrating diaphragm is pressed. When the lower surface of the vibrating diaphragm rests against the top end of the protruding pole, a sound of a high frequency can be heard by the stethoscope head.

A pore for protruding pole is arranged in the sound collecting surface, and the bottom end of the protruding pole is fixed in the pore for protruding pole. A protruding pole may be arranged on the bottom of the sound guiding hole.

A multi-audio stethoscope head includes a head body, a vibrating diaphragm and a fastener; a sound guiding hole is provided in the head body; the fastener includes an axial through hole, a fastener sidewall configured for attaching to the head body and a diaphragm pressing portion configured for attaching the vibrating diaphragm to the head body; the vibrating diaphragm includes an upper surface and a lower surface and is arranged between the diaphragm pressing portion and the head body; where a sound enhancing ring is disposed between the vibrating diaphragm and the head body and/or a sound enhancing ring is disposed between the vibrating diaphragm and the diaphragm pressing portion, and the sound enhancing ring is at least partially positioned at the outer side of the through hole of the fastener.

A portion of contact between the sound enhancing ring and the vibrating diaphragm is positioned between a sidewall of the through hole of the fastener and a radially inner face of the fastener sidewall. The lower surface of the vibrating diaphragm between the sound enhancing ring and a radially inner face of the fastener sidewall is spaced from the upper surface of the head body at a radially outer side of the sound enhancing ring.

Alternatively, after the vibrating diaphragm, the fastener and the sound enhancing ring(s) are cooperatively fixed, a gap is present between the lower surface of the vibrating diaphragm at a radially outer side of the sound enhancing ring and the upper surface of the head body, or a gap is present between the upper surface of the vibrating diaphragm at a radially outer side of the sound enhancing ring and the diaphragm pressing portion of the fastener.

The sound enhancing ring is made by an elastomer.

In addition, the sound enhancing ring and the head body may fit in a way that: an annular groove is provided in the upper surface of the head body to receive the sound enhancing ring, and at least a part of the sound enhancing ring extends out of the annular groove.

It is possible that the portion of contact between the sound enhancing ring and the lower surface of the vibrating diaphragm may be perpendicular to the portion of contact between the upper surface of the vibrating diaphragm and the diaphragm pressing portion.

It is also possible that the portion of contact between the sound enhancing ring and the lower surface of the vibrating diaphragm may correspond to the portion of contact between the upper surface of the vibrating diaphragm and the diaphragm pressing portion in the vertical direction.

In the above solutions, the vibrating diaphragm is a flat sheet made by a single material that has a uniform thickness.

In the above solutions, an edge of the vibrating diaphragm is free of elastic coating.

In the above solutions, the sound enhancing ring may be disposed on the upper or lower surface of an edge region of the vibrating diaphragm.

In the above solutions, the sound enhancing ring, which is separate from the vibrating diaphragm, may be disposed at the edge region of the vibrating diaphragm.

Another object of the present disclosure is to provide a method for hearing multiple audio frequencies, which is applicable to the stethoscope head, where at least one protruding pole is provided on the sound collecting surface of the head body, the vibrating diaphragm is fixed to the head body by the diaphragm pressing portion of the fastener and defines a sound collecting cavity together with the sound collecting surface, and the protruding pole is positioned in the sound collecting cavity, below the lower surface of the vibrating diaphragm. With the use of the stethoscope head, a low-frequency sound is heard when the lower surface of the vibrating diaphragm is spaced from the top end of the protruding pole, and a high-frequency sound is heard when the vibrating diaphragm is pressed to rest against the top end of the protruding pole. However, the sound collecting cavity is not divided into disconnected compartments in both of hearing the high-frequency sound and hearing the low-frequency sound.

The top end of the axial protruding pole provided on the sound collecting surface is below the top portion of the sound enhancing ring, the protruding pole is located remotely from the outer side of the head body, and the stethoscope head may be pressed towards a sound source during the auscultation so that the central part of the vibrating diaphragm of the stethoscope head concaves inwards and rests against the top portion of the protruding pole, thereby changing the amplitude of the vibrating diaphragm to enable hearing of a varied audio frequency. By this way of hearing multiple audio frequencies, the following benefits are achieved.

In hearing multiple audio frequencies by the inventive stethoscope head, for example in switching between hearing of a high-frequency sound and hearing of a low-frequency sound, the effective diameter of the sound collecting cavity is not decreased, thus ensuring the volume of the heard sound. However in the prior art, when switching from hearing of a low-frequency sound to hearing of a high-frequency sound by the existing stethoscope head, the effective diameter of the sound collecting cavity is decreased, resulting in relatively lowered volume of the heard sound; in addition, a high-frequency sound collecting ring is necessarily provided on the sound collecting surface of the multi-audio or high-frequency audio stethoscope head in the prior art, but such high-frequency sound collecting ring is not required by the inventive stethoscope head for even more clearly hearing high-frequency sounds.

In a stethoscope head capable of hearing multiple audio frequencies by its single side, the vibrating diaphragm has a composite structure in which an elastic surrounding ring allowing for up and down movements of the sheet-like vibrating diaphragm is provided at an edge of the vibrating diaphragm, where the surrounding ring is coated on and internally formed with the edge of the vibrating diaphragm which is hard. On one hand, such composite structure of the vibrating diaphragm is complicated in manufacturing and costly, on the other hand, due to the elastic surrounding ring attached to the edge of the sheet-like hard vibrating diaphragm, the property of the vibrating diaphragm is changed, resulting in unclear conducted sound. In the present disclosure, it is not required to add an elastic surrounding ring allowing for up and down movements of the sheet-like vibrating diaphragm to an edge of the vibrating diaphragm, the conducted sound is clearer than that in the prior art.

In the present disclosure, no additional elastic material is coated on the edge of the vibrating diaphragm, thus the loss of sound energy of propagating sound waves at an interface of different combined materials is prevented in the inventive vibrating diaphragm made of a single material.

In the present disclosure, no additional elastic material is coated on the edge of the vibrating diaphragm, thus the absorbing of sound energy by the elastic material due to the sound absorbing property of the elastic material is avoided.

In the prior art, the elastic material attached to the edge of the vibrating diaphragm is inconvenient for cleaning but is vulnerable to breeding bacterium. In the present disclosure, however, no elastic material is attached to the vibrating diaphragm, which is hence easy for cleaning.

In the prior art, the elastic material attached to the edge of the vibrating diaphragm is vulnerable to fatigue, which significantly reduces the lifetime of the vibrating diaphragm, compared to which the lifetime of the vibrating diaphragm in the present disclosure is longer.

In the prior art, the elastic material attached to the edge of the vibrating diaphragm is vulnerable to fatigue, which affects the switching between hearing of a high-frequency sound and hearing of a low-frequency sound in use. In the present disclosure, however, no composite material is attached to the edge of the vibrating diaphragm and hence the fatigue of the vibrating diaphragm is avoided.

In the present disclosure, the elastic sound enhancing ring and the vibrating diaphragm are made individually, that is, the vibrating diaphragm is made of a single material. As a result of such sound enhancing structure, the good sound conducting performance is ensured, and meanwhile refraction or scattering of the propagating sound waves is avoided because the vibrating diaphragm is made of a single material, so that the loss of the sound energy is small, the sound conducting property of the vibrating diaphragm is maintained, and the heard sound is clear without distortion.

The inventive vibrating diaphragm would concave even if a small force is applied to its central part, so that the vibrating diaphragm rests against the protruding pole and hence the resonant wavelength of the vibrating diaphragm is changed, meanwhile the vibrating diaphragm is more tensioned, that is, the tension of the vibrating diaphragm is changed, the wavelength is changed and the audio frequency as heard is changed, but the size of the sound collecting surface is not changed. In the prior art, the size of the sound collecting surface is changed significantly in hearing different audio frequencies, and hence the volume of the heard sound is reduced.

If the protruding pole is arranged in the sound guiding hole, spiral resonance occurs to sound waves at the outside of the protruding pole, thereby increasing the volume of the sound as heard.

In the drawings:
1 head body; 11 sound collecting surface; 12 annular groove;
 13 annular protrusion;
14 upper surface; 15 fixing face; 16 sound guiding hole;
161 sidewall of sound guiding hole; 162 bottom of sound guiding hole; 17 stopper structure;
18 pore for protruding pole;
2 vibrating diaphragm; 21 upper surface; 22 lower surface; 23 edge;
231 lower peripheral surface of vibrating diaphragm;
232 upper peripheral surface of vibrating diaphragm; 24 central portion; 25 side face;
3 fastener; 31 fastener sidewall; 311 inner face of fastener sidewall;
32 diaphragm pressing portion; 321 lower surface of diaphragm pressing portion;
33 through hole; 331 sidewall of through hole; 34 annular groove;
4 sound enhancing ring; 41 top portion; 4a sound enhancing ring; 4b sound enhancing ring;
41a top portion; 5, 5a, 5b, 5c gap; 51 sound collecting cavity;
6 protruding pole; 61 top end; 71, 71a, 71b, 72, 72a portion of contact;
8 rotary shaft; 9 support member
D1 diameter of stethoscope body; D2 maximum diameter of sound collecting surface.

DETAILED DESCRIPTION

The present disclosure will be further described hereinafter in combination with the accompanying drawings. The provided embodiments of the present disclosure are merely shown as preferable, without limiting the scope of the present invention. In the contrary, the present disclosure is intended to comprise various modifications and equivalent arrangements in the scope of the present invention.

Embodiment 1: The present disclosure is described below in detail in combination with FIGS. 1 to 3 and provides a stethoscope head including a head body 1, a vibrating diaphragm 2, a fastener 3 and a sound enhancing ring 4.

Figure 1:
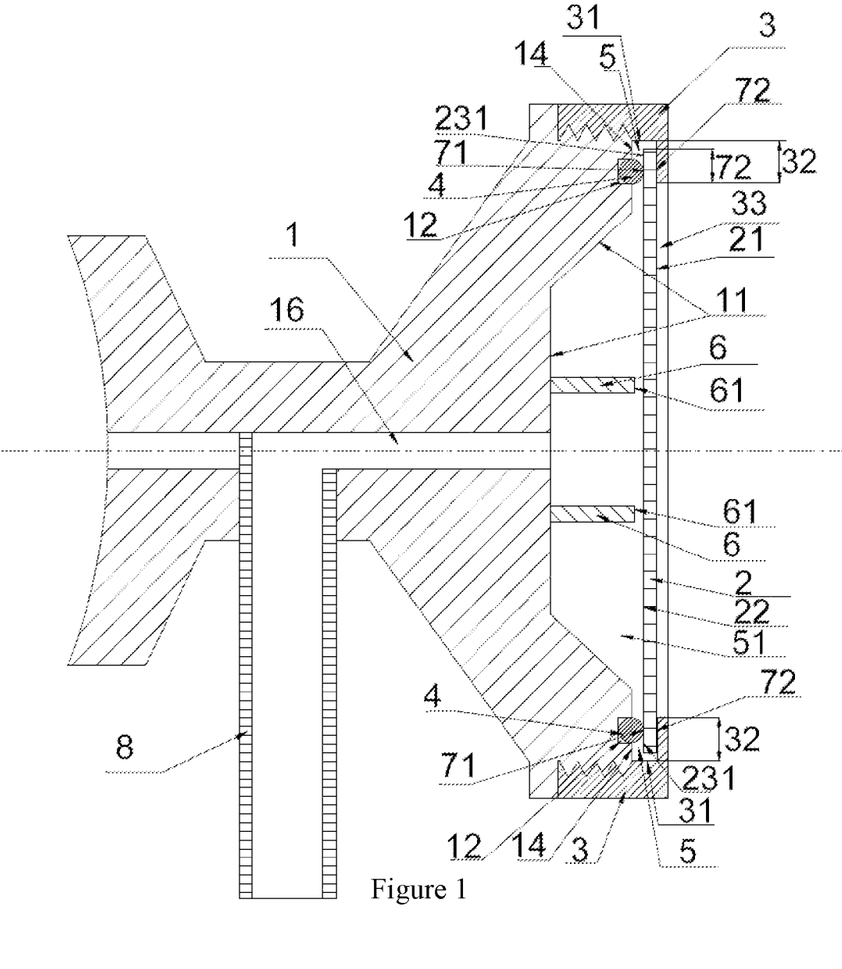
FIG. 1 is a schematic diagram of an inventive stethoscope head.
Figure 2:
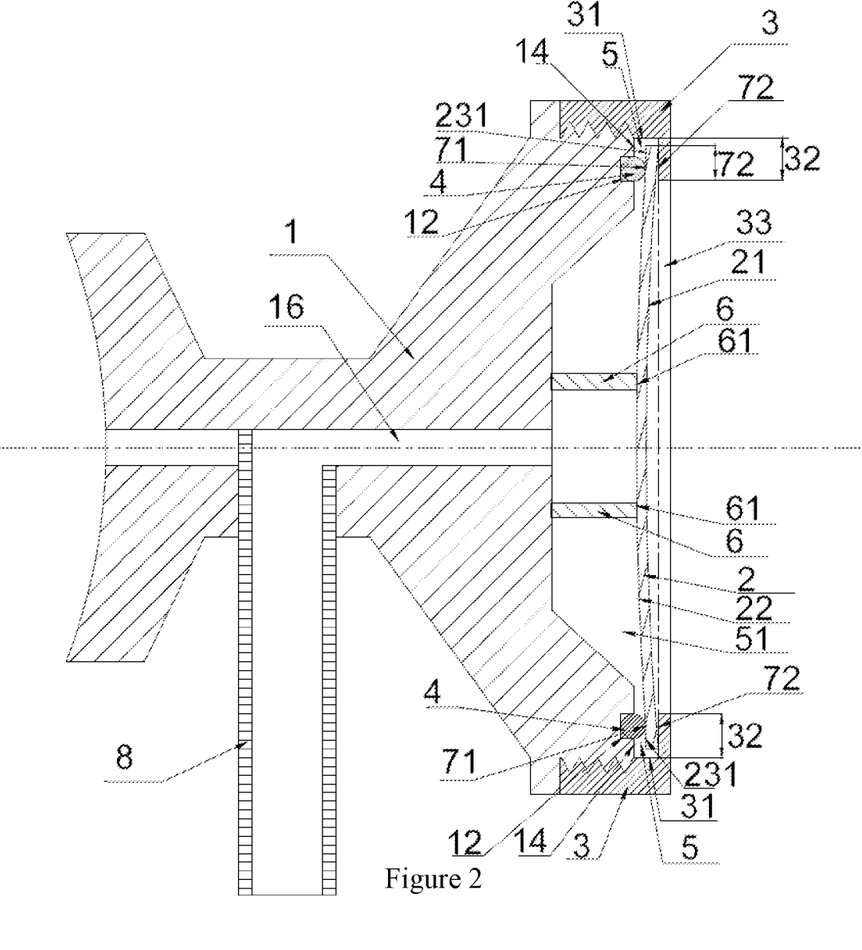
FIG. 2 is another schematic diagram of the inventive stethoscope head.
Figure 3:
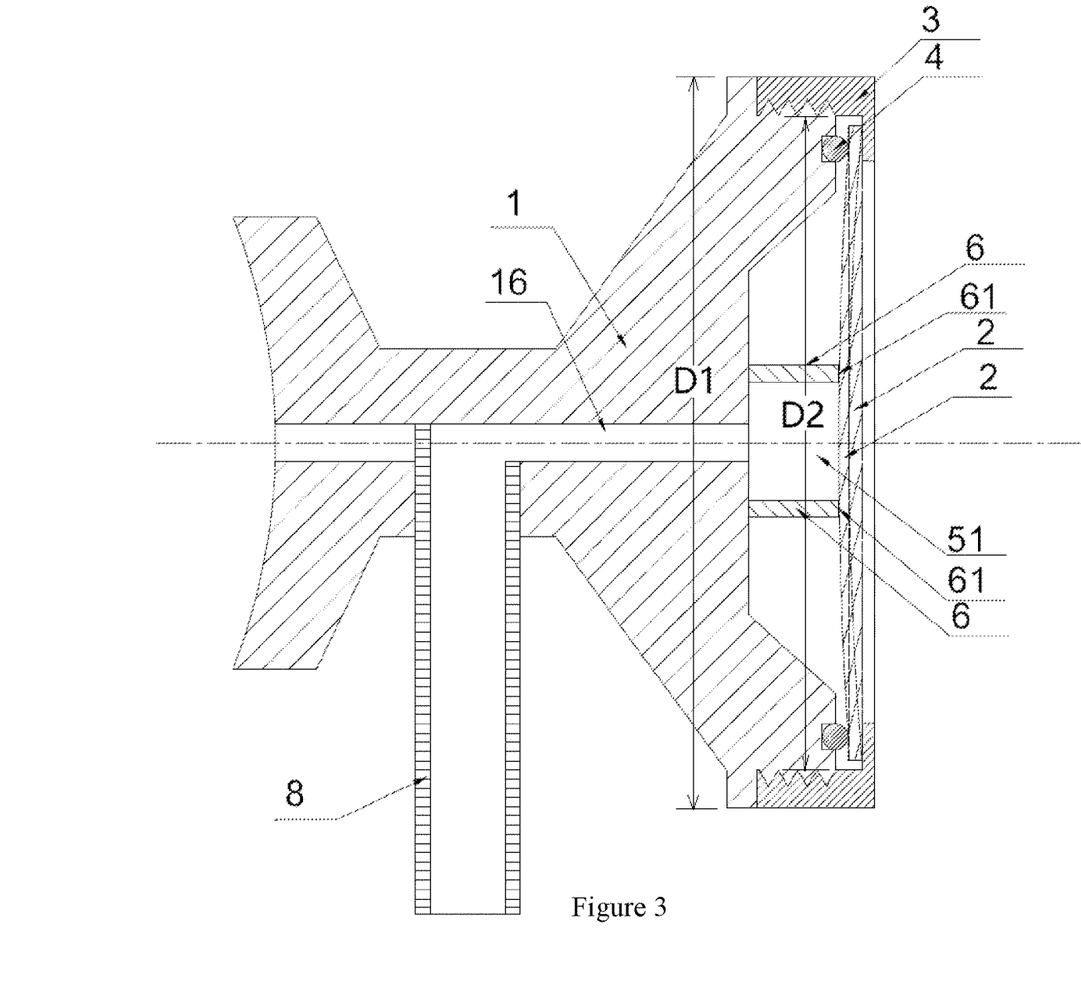
FIG. 3 is still another schematic diagram of the inventive stethoscope head.

The head body 1 is provided with a sound collecting surface 11 and a sound guiding hole 16 configured for conducting sounds to a rotary shaft, and an annular groove 12 for holding a sound enhancing ring 4 is provided on an upper surface 14 of the head body 1. Here, four protruding poles 6 are arranged on the sound collecting surface 11. These protruding poles 6 may be fixed to the head body 1 via threads, and top ends 61 of the protruding poles 6 are under the vibrating diaphragm 2 and lower than a portion of contact 71 between the sound enhancing ring 4 and the vibrating diaphragm 2.

The fastener 3, which is L-shaped, includes a fastener sidewall 31 which is configured for attaching to the head body 1 and an inner face 311 of which is provided with threads matching with the head body 1, a diaphragm pressing portion 32 configured for pressing the vibrating diaphragm 2 and a through hole 33 formed in the diaphragm pressing portion 32.

The vibrating diaphragm 2 includes an upper surface 21 and a lower surface 22.

The vibrating diaphragm 2 is disposed between the L-shaped fastener 3 and the head body 1 by using the fastener 3, and the lower surface 22 of the vibrating diaphragm 2 and the sound collecting surface 11 together define a sound collecting cavity 51.

An annular sound enhancing ring 4 is disposed between the lower surface 22 of the vibrating diaphragm 2 and the upper surface 14 of the head body 1, with the sound enhancing ring 4 being placed in the annular groove 12 of the head body 1 and a top portion 41 of the sound enhancing ring 4 extending out of the annular groove 12.

A portion of contact 71 between the sound enhancing ring 4 and the lower surface 22 of the vibrating diaphragm 2 is positioned right below the diaphragm pressing portion 32, i.e., within the range of the projection of the diaphragm pressing portion 32 onto the horizontal plane. The portion of contact 71 between the sound enhancing ring 4 and the lower surface 22 of the vibrating diaphragm 2 and a portion of contact 72 between the upper surface 21 of the vibrating diaphragm 2 and the diaphragm pressing portion 32 are subjected to forces in the corresponding vertical directions, respectively.

In order to hear a low-frequency sound by the stethoscope head, the vibrating diaphragm 2 is placed in contact with a sound source such as an organ, so that activity sounds of the organ are transferred to the sound collecting cavity 51 via the vibrating diaphragm 2 and then conducted through the sound guiding hold 16 and further through the rotary shaft.

In order to hear a high-frequency sound by the stethoscope head, the head body 1 is pressed towards the sound source so that the lower surface 22 of the vibrating diaphragm 2 rests against top ends 61 of the protruding poles 6, thus the vibrating property of the vibrating diaphragm 2 is changed to thereby hear the high-frequency sound.

Embodiment 2: The present disclosure is further described in combination with FIG. 4 and provides a stethoscope head which includes a head body 1, a vibrating diaphragm 2, a fastener 3 and sound enhancing rings 4.

Figure 4:
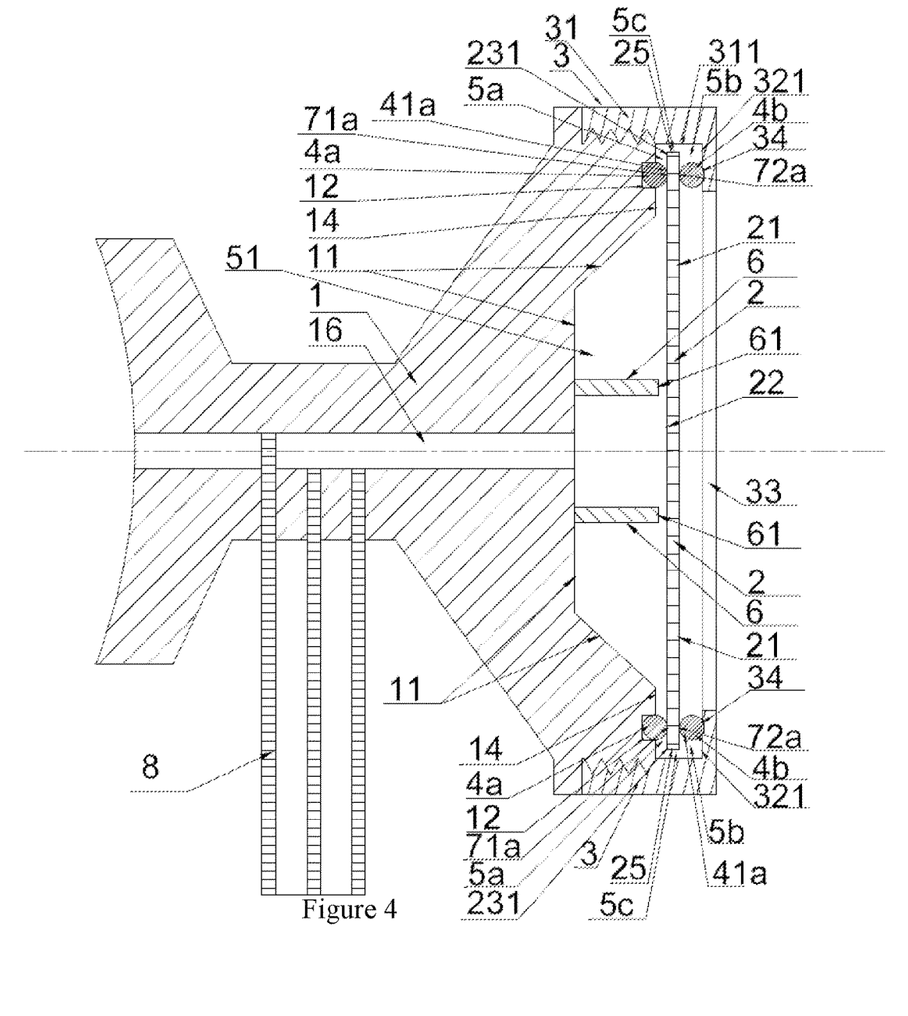
FIG. 4 is a schematic diagram of an inventive stethoscope head provided with two sound enhancing rings.

The head body 1 is provided with a sound collecting surface 11, and a sound guiding hole 16 configured for conducting sounds to a rotary shaft, and an annular groove 12 configured for holding the sound enhancing rings 4. The fastener 3, which is L-shaped, includes a fastener sidewall 31 which is configured for attaching to the head body 1, a diaphragm pressing portion 32 configured for pressing the vibrating diaphragm 2 and a through hole 33 formed in the diaphragm pressing portion 32. An inner face 311 of the fastener sidewall 31 is provided with threads matching with the head body 1.

The vibrating diaphragm 2 includes an upper surface 21 and a lower surface 22.

The vibrating diaphragm 2 is disposed between the L-shaped fastener 3 and the head body 1 by using the fastener 3, and the lower surface 22 of the vibrating diaphragm 2 and the sound collecting surface 11 together define a sound collecting cavity 51.

An annular sound enhancing ring 4 is disposed between the lower surface 22 of the vibrating diaphragm 2 and the head body 1, with the sound enhancing ring 4 being placed in the annular groove 12 of the head body 1 and a top portion 41 of the sound enhancing ring 4 extending out of the annular groove 12.

A portion of contact 71 between the sound enhancing ring 4 and the lower surface 22 of the vibrating diaphragm 2 is positioned right below the diaphragm pressing portion 32. The portion of contact 71 between the sound enhancing ring 4 and the lower surface 22 of the vibrating diaphragm 2 and a portion of contact 72 between the upper surface 21 of the vibrating diaphragm 2 and the diaphragm pressing portion 32 are subjected to forces in the corresponding vertical directions, respectively.

A gap 5 is present under the lower surface of the vibrating diaphragm 2 between the radially outer side of the sound enhancing ring 4 (i.e., the outer side of the portion of contact 71 between the sound enhancing ring 4 and the vibrating diaphragm 2) and the inner face 311 of the fastener sidewall 31, that is, the lower surface of the vibrating diaphragm 2 that is at the outer side of the portion of contact 71 is not attached, in other words, the lower peripheral surface 231 of vibrating diaphragm 2 at the edge 23 of the vibrating diaphragm 2 is spaced from the upper surface 14 by the gap 5.

The portion of contact 71 between the top portion 41 of the sound enhancing ring 4 and the vibrating diaphragm 2 is always positioned below the diaphragm pressing portion 32 of the fastener 3. A top portion 41 of a sound enhancing ring 4 may be in contact with the lower surface of the diaphragm pressing portion, i.e., a surface of the diaphragm pressing portion that is in contact with the vibrating diaphragm.

In the case where the vibrating diaphragm 2 is in contact with the top portion 41 of the sound enhancing ring 4, the lower surface 22 of the vibrating diaphragm 2 at the inner side of the sound enhancing ring 4 is spaced from the sound collecting surface 11, and the lower peripheral surface 231 of vibrating diaphragm 2 at the outer side of the sound enhancing ring 4 is spaced from the upper surface 14 of the head body 1.

As shown in FIG. 4, it is possible to provide two sound enhancing rings, one of which 4a is located between the lower surface 22 of the vibrating diaphragm and the sound collecting surface 11 of the head body 1, and the other of which 4b is located between the upper surface 21 of the vibrating diaphragm and the lower surface of the diaphragm pressing portion of the fastener 3. The lower peripheral surface of vibrating diaphragm; 231 is spaced from the upper surface 14 of the head body 1 by a gap 5.

A portion of contact 71a between the sound enhancing ring 4a and the lower surface 22 of the vibrating diaphragm 2 is right opposite to a portion of contact 71b between the sound enhancing ring 4b and the upper surface 21 of the vibrating diaphragm 2, and all of the portions of contact 71a and 71b and a portion of contact 72a between the sound enhancing ring 4b and the lower surface of the diaphragm pressing portion are positioned right below the diaphragm pressing portion 32 of the fastener 3, i.e., within the range of the projection of the diaphragm pressing portion 32 onto the horizontal plane.

Embodiment 3: The present disclosure is further described in combination with FIG. 5 and provides a stethoscope head which includes a head body 1, a vibrating diaphragm 2, and a fastener 3.

Figure 5:
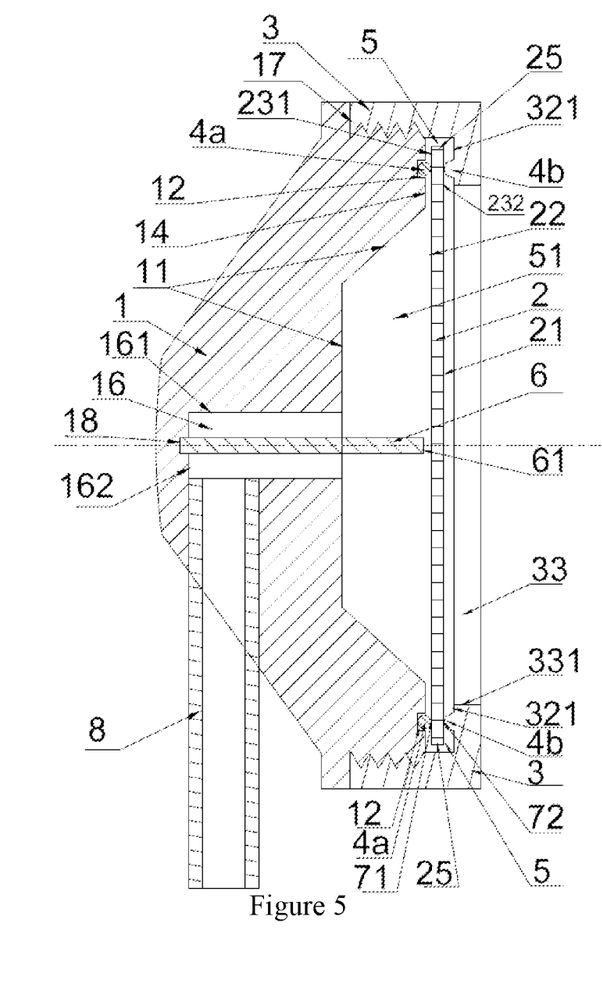
FIG. 5 is a schematic diagram of an inventive stethoscope head provided with two sound enhancing rings, one of which is integrally formed with a fastener of the stethoscope head.

The head body 1 is provided with a sound collecting surface 11, a sound guiding hole 16 configured for conducting sounds to a rotary shaft, an annular groove 12 configured for holding a sound enhancing ring 4a, and an upper surface 14.

The fastener 3, which is L-shaped, includes a fastener sidewall 31 which is configured for attaching to the head body 1, a diaphragm pressing portion 32 configured for pressing the vibrating diaphragm 2 and a through hole 33 formed in the diaphragm pressing portion 32. An inner face 311 of the fastener sidewall 31 is provided with threads matching with the head body 1. A sound enhancing ring 4b is provided on the lower surface 321 of the diaphragm pressing portion 32 and formed integrally with the diaphragm pressing portion 32 using the same material.

The vibrating diaphragm 2 includes an upper surface 21 and a lower surface 22.

The vibrating diaphragm 2 is disposed between the L-shaped fastener 3 and the head body 1 by using the fastener 3. Particularly, the vibrating diaphragm 2 is positioned between the sound enhancing ring 4a and the sound enhancing ring 4b. The lower surface 22 of the vibrating diaphragm 2 is in contact with a top portion of the sound enhancing ring 4a, and the upper surface 21 of the vibrating diaphragm 2 is in contact with a bottom portion of the sound enhancing ring 4b.

The lower surface 22 of the vibrating diaphragm 2, the sound enhancing ring 4a, the upper surface 14, the sound collecting surface 11, a sidewall of sound guiding hole 161, and the bottom of sound guiding hole 162 together define a sound collecting cavity 51.

The annular sound enhancing ring 4a, which is disposed between the lower surface 22 of the vibrating diaphragm 2 and the head body 1, is placed in the annular groove 12 of the head body 1, with a top portion 41 of the sound enhancing ring 4a extending out of the annular groove 12.

The annular groove 12 may have a height of 0.7 mm and a width of 1.1 mm, and the sound enhancing ring 4 may have the maximum diameter of 1.0 mm.

A portion of contact 71 between the sound enhancing ring 4a and the vibrating diaphragm 2 is positioned right below the diaphragm pressing portion 32. Further, the portion of contact 71 between the sound enhancing ring 4a and the lower surface 22 of the vibrating diaphragm 2 and a portion of contact 72 between the sound enhancing ring 4b and the upper surface 21 of the vibrating diaphragm 2 are opposite to each other along the longitudinal direction of the vibrating diaphragm 2.

Both of the sound enhancing rings 4a and 4b are at the outer side of the sidewall 331 of the through hole of the fastener 3, and both of the portions of contact 71 and 72 are positioned between a longitudinal extension plane of the sidewall 331 of the through hole and a longitudinal extension plane of the inner face 311 of the fastener sidewall.

A gap 5 is present under the lower peripheral surface 231 of the vibrating diaphragm 2 between the radially outer side of the sound enhancing ring 4 (i.e., the outer side of the portion of contact 71 between the sound enhancing ring 4 and the vibrating diaphragm 2) and the inner face 311 of the fastener sidewall 31, that is, the lower peripheral surface 231 of the vibrating diaphragm 2 that is at the outer side of the portion of contact 71 is not attached, in other words, the lower peripheral surface 231 of vibrating diaphragm 2 at the edge 23 of the vibrating diaphragm 2 is spaced from the fixing face 15 by the gap 5.

At the outer side of the sound enhancing ring 4b, a gap 5 is present above the upper peripheral surface 232 of the vibrating diaphragm 2 between the portion of contact 72 between the bottom portion of the sound enhancing ring 4b and the vibrating diaphragm 2 and the inner face 311 of the fastener sidewall 31, that is, the upper peripheral surface 232 of the vibrating diaphragm 2 that is at the outer side of the portion of contact 72 is not attached, in other words, the upper peripheral surface 232 of vibrating diaphragm 2 at the edge 23 of the vibrating diaphragm 2 is spaced from the lower surface 321 of the diaphragm pressing portion by the gap 5.

In the case where the vibrating diaphragm 2 is in contact with the top portion 41 of the sound enhancing ring 4a, the lower surface 22 of the vibrating diaphragm 2 at the inner side of the sound enhancing ring 4a is spaced from the sound collecting surface 11, and the lower peripheral surface 231 of the vibrating diaphragm at the outer side of the sound enhancing ring 4a is spaced from the upper surface 14 of the head body 1.

The sound enhancing ring 4a is placed in the annular groove 12 of the head body 1. After the vibrating diaphragm 2 is fixed between the sound enhancing ring 4a and the sound enhancing ring 4b of the fastener 3, the vibrating diaphragm 2 is maintained flat without bending.

A pore for protruding pole 18 may be provided in the bottom of sound guiding hole 162 of the sound guiding hole 16.

The bottom of the protruding pole 6 is fixed to the pore for protruding pole 18. The protruding pole 6 may be fixed to the pore for protruding pole 18 by interference fit, or by adhesion, or in a threaded manner by using internal threads provided in the pore for protruding pole 18 and external threads provided around the bottom of the protruding pole 6.

The top end 61 of the protruding pole 6 may be spaced from the lower surface 22 of the vibrating diaphragm 2 by 0.4 mm. The protruding pole 6 may have a columnar shape with a diameter of 2 mm and a height of 7.5 mm, the sound guiding hole 16 may have a diameter of 6 mm and a depth of 6.3 mm, and the central axis of the protruding pole 6 may be distanced from the edge of the sound collecting surface by 21 mm. Preferably, a distance from the protruding pole 6 to the center of the sound guiding hole 16 is no more than 50% of the radius of the sound collecting cavity 51.

To hear varied audio frequency by the stethoscope head, the head body 1 is pressed towards the sound source so that the lower surface 22 of the vibrating diaphragm 2 rests against the top end 61 of the protruding pole 6. Regardless of the switching between audio frequencies intended to be heard, the diameter of the maximum effective sound collecting portion of the sound collecting surface 11 is maintained unchanged.

Figure 6:
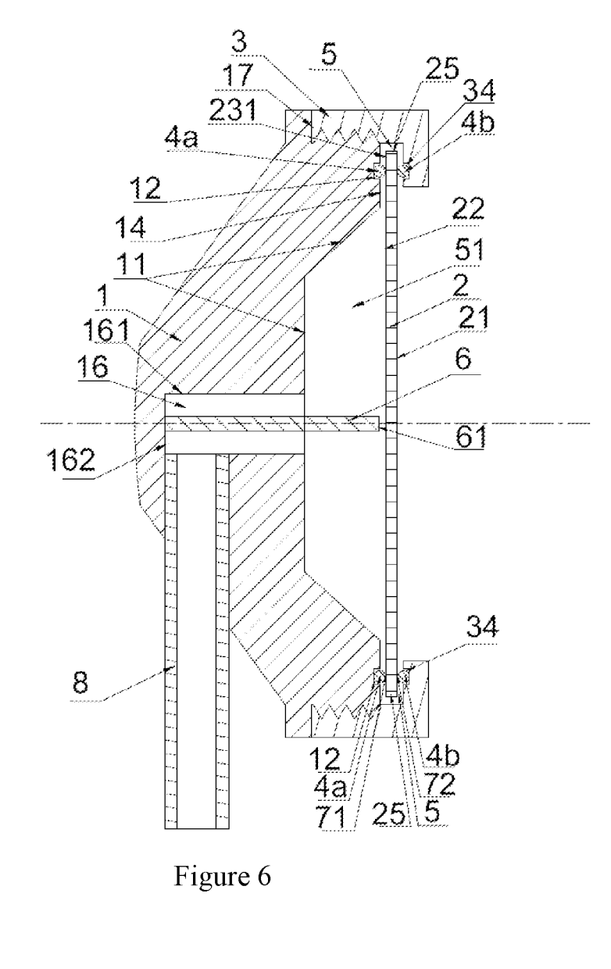
FIG. 6 is a schematic diagram of an inventive single-sided stethoscope head provided with two sound enhancing rings.
Figure 7:
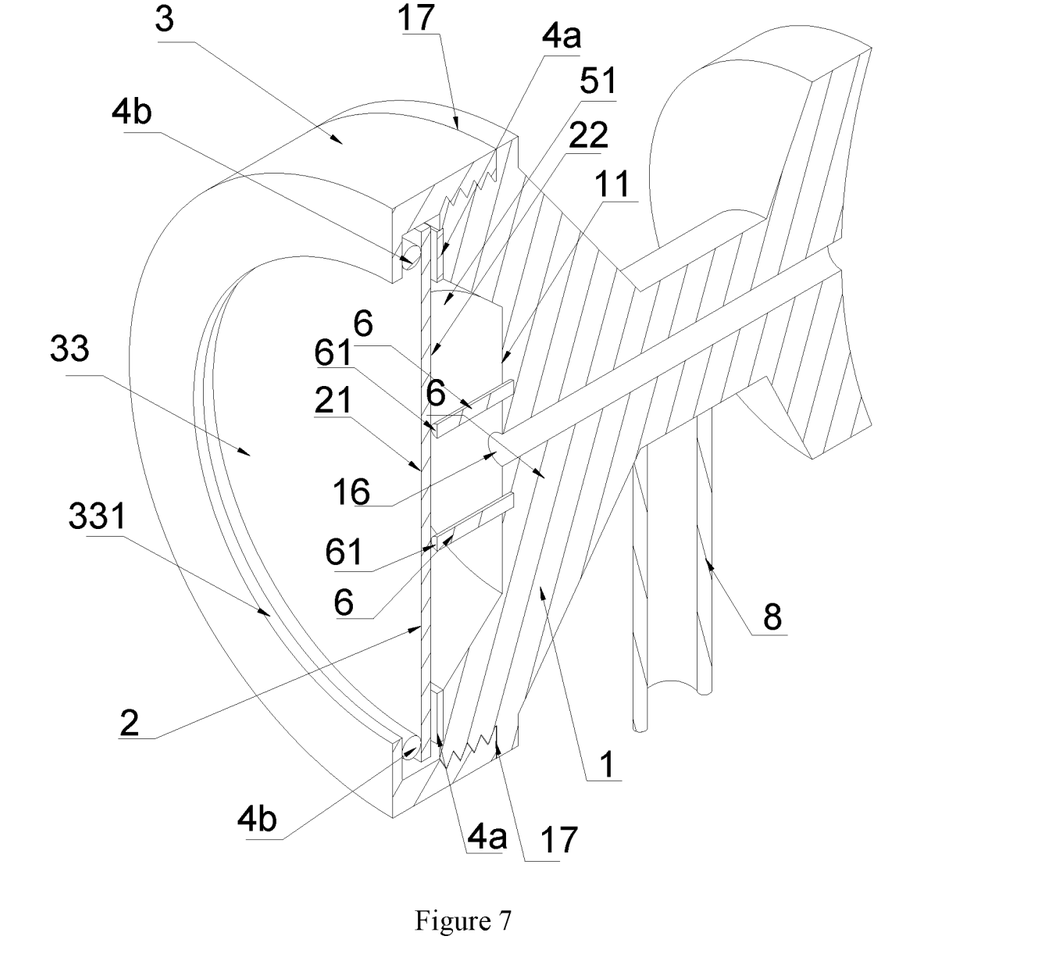
FIG. 7 is a schematic perspective section view of an inventive stethoscope head provided with two sound enhancing rings.
Figure 8:
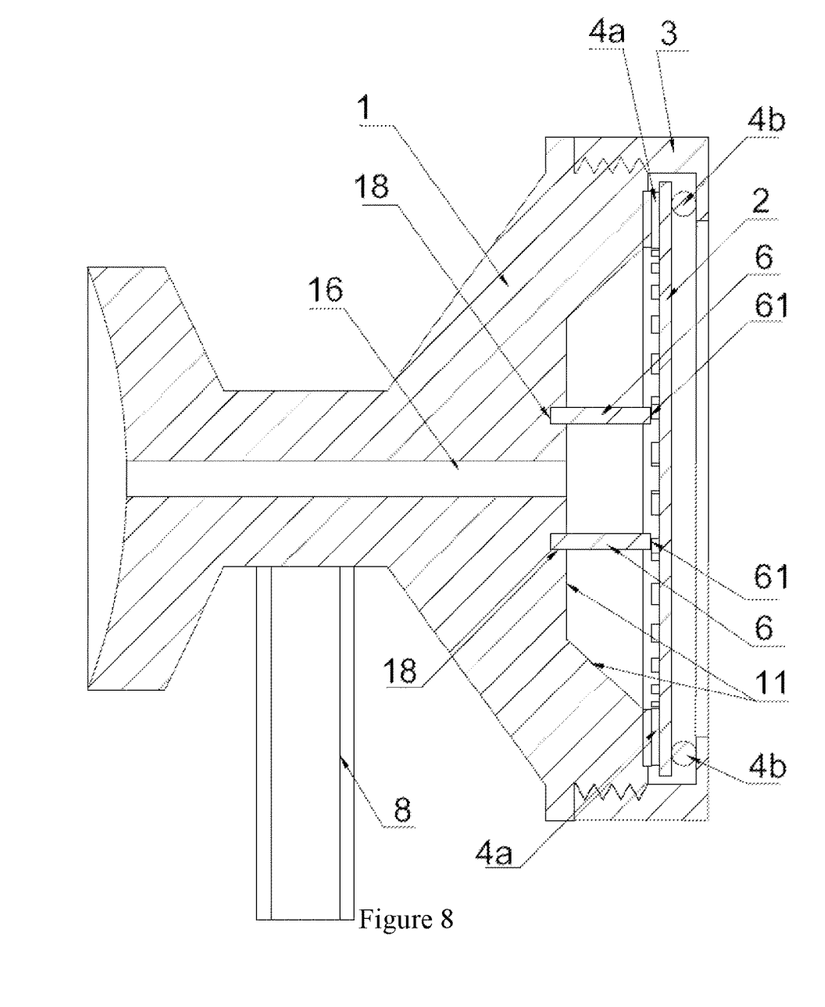
FIG. 8 is a schematic section view of the stethoscope head shown in FIG. 7.
Figure 9:
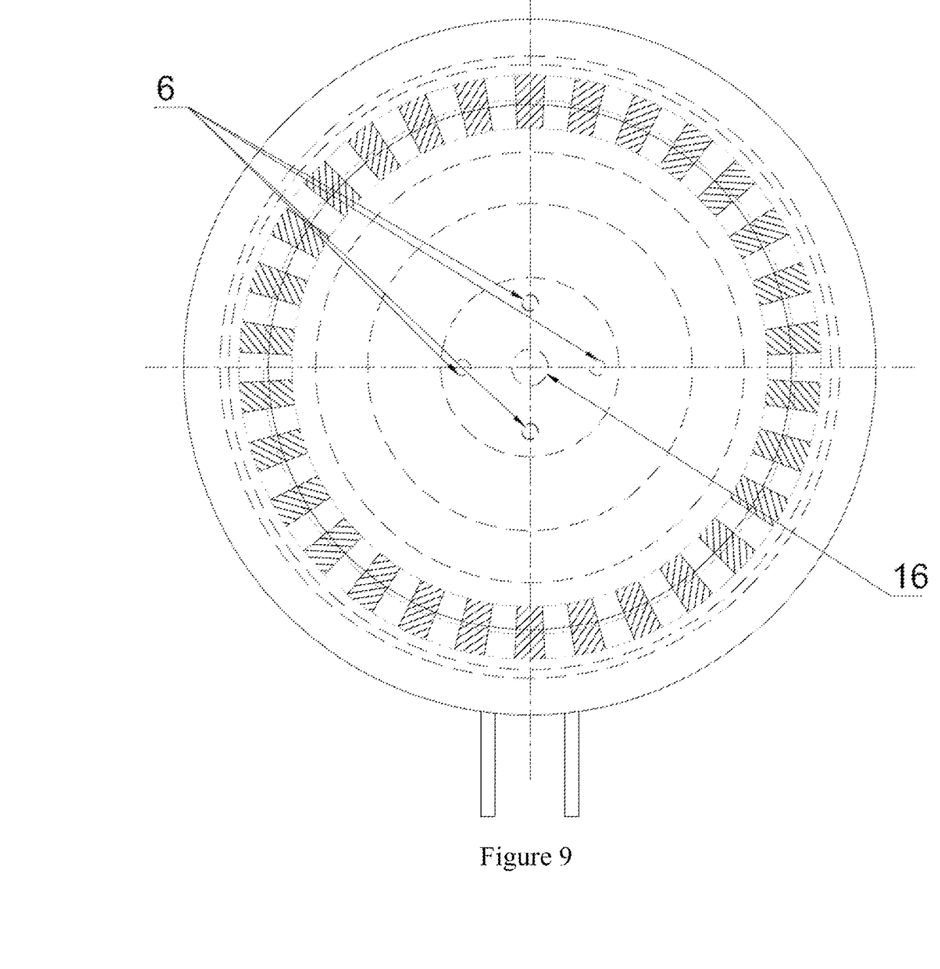
FIG. 9 is a schematic right view of the stethoscope head shown in FIG. 7.
Figure 10:
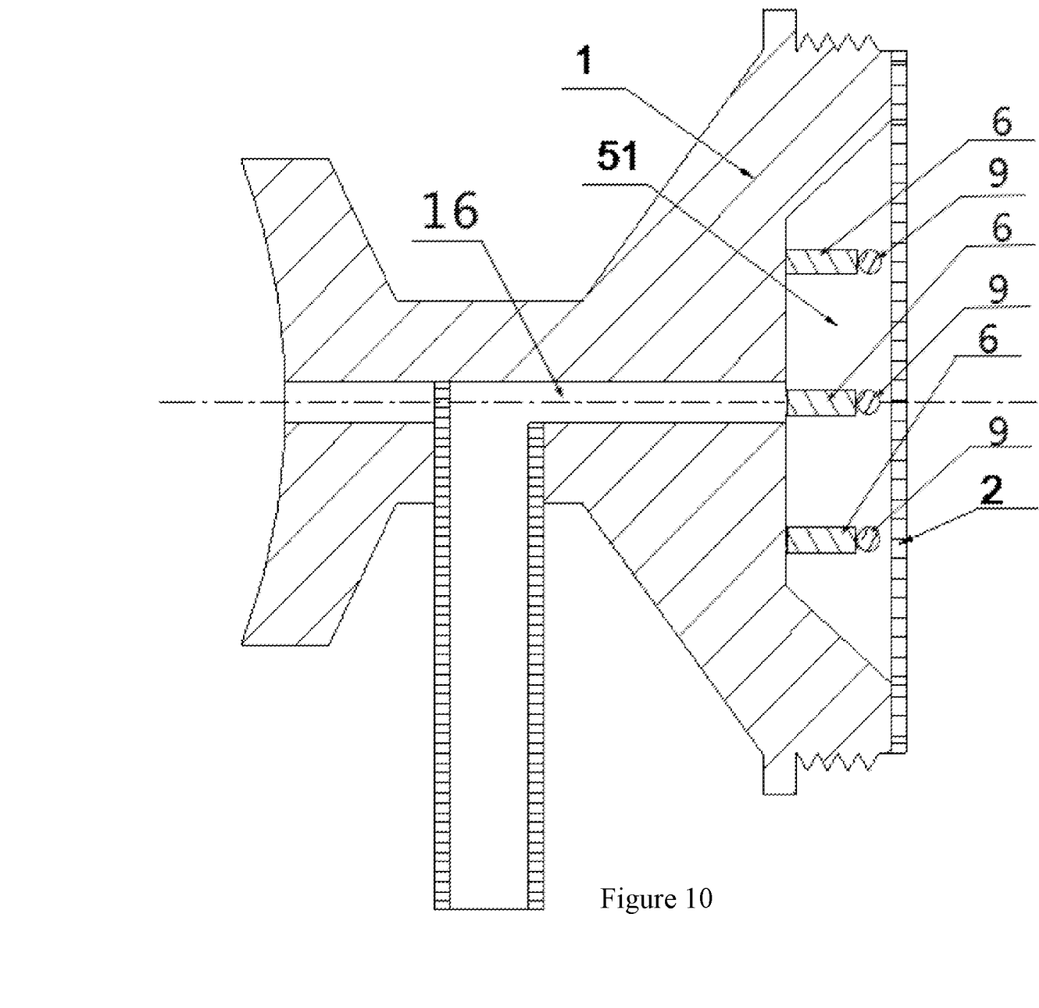
FIG. 10 is a schematic diagram of still another inventive stethoscope head.
Figure 11:
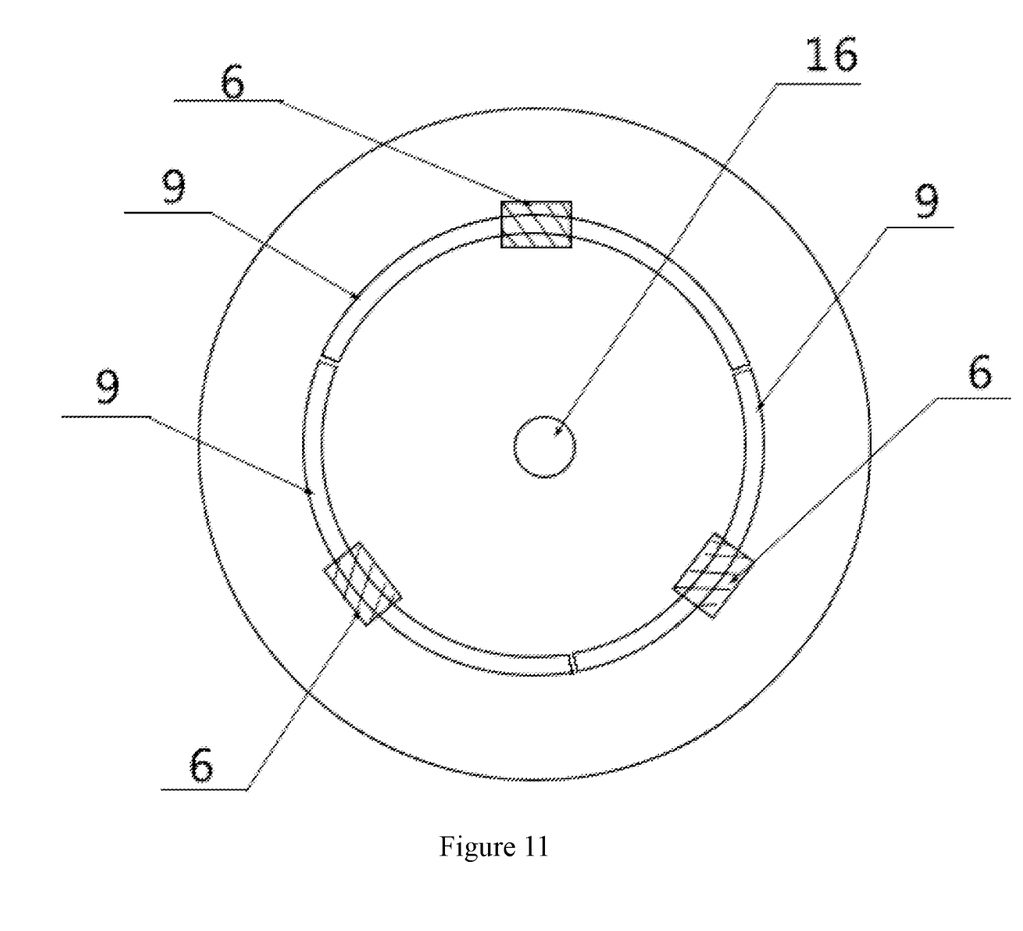
FIG. 11 is a schematic right view of the stethoscope head shown in FIG. 10.

In the above embodiments, the sound enhancing ring 4b and the fastener 3 may be individually formed (as shown in FIG. 6), and the sound enhancing ring 4b is placed in an annular groove 34 formed in the lower surface 321 of the diaphragm pressing portion of the fastener 3.

In the above embodiments, when the upper surface 21 of the vibrating diaphragm 2 is pressed so that the vibrating diaphragm 2 is deformed downwards, the lower surface 22 of the vibrating diaphragm 2 contacts the top end 61 of the protruding pole 6, and thus a vibrating amplitude of the vibrating diaphragm 2 is changed and a varied audio frequency (e.g., high-frequency sound) is heard.

What is claimed is:

1. A multi-audio stethoscope head, comprising:
a head body;
a vibrating diaphragm; and
a fastener;
a fastener sidewall configured for attaching to the head body; and
a diaphragm pressing portion configured for attaching the vibrating diaphragm to the head body,
wherein a sound collecting surface is provided on the head body, a sound guiding hole is provided in the sound collecting surface, and the fastener includes an axial through hole,
wherein the vibrating diaphragm is disposed between the diaphragm pressing portion and the head body, and includes a lower surface facing the sound collecting surface of the head body and an upper surface opposite to the lower surface,
wherein a sound collecting cavity is defined between the vibrating diaphragm and the sound collecting surface, wherein at least one protruding pole which protrudes towards the vibrating diaphragm is arranged on the sound collecting surface of the head body at an radially inner side of the through hole of the fastener, and the vibrating diaphragm, when not subjected to an external force, is spaced from the protruding pole so that a sound of a first frequency is heard by the stethoscope head, and
wherein when the vibrating diaphragm is pressed to concave inwards and rest against a top end of the protruding pole, the sound collecting cavity is not divided into a plurality of disconnected compartments and a sound of a second frequency different from the first frequency is heard by the stethoscope head.

2. The multi-audio stethoscope head of claim 1, wherein, the protruding pole and the head body are individually made and matches with each other.

3. The multi-audio stethoscope head of claim 1, wherein, a plurality of the protruding poles are present, and the protruding poles are at least partially spaced.

4. The multi-audio stethoscope head of claim 1, wherein, the protruding pole is arranged on a bottom of the sound guiding hole.

5. The multi-audio stethoscope head of claim 1, wherein, the vibrating diaphragm is fixed to the head body by the diaphragm pressing portion of the fastener, the protruding pole is within the sound collecting cavity.

6. The multi-audio stethoscope head of claim 1, wherein, a sound enhancing ring is disposed between the vibrating diaphragm and the head body and/or a sound enhancing ring is disposed between the vibrating diaphragm and the diaphragm pressing portion, and the sound enhancing ring is at least partially positioned at a radially outer side of the through hole of the fastener.

7. The multi-audio stethoscope head of claim 6, wherein, the sound enhancing ring is connected or engaged with the upper or lower surface of the vibrating diaphragm to form a portion of contact, which is at least partially positioned between a longitudinal extension plane of a sidewall of the through hole and a longitudinal extension plane of the fastener sidewall or an inner face of the fastener sidewall.

8. The multi-audio stethoscope head of claim 1, wherein, a sound enhancing ring is disposed between the lower surface of the vibrating diaphragm and the head body and/or between the upper surface of the vibrating diaphragm and the fastener, and a portion of contact between the sound enhancing ring and the vibrating diaphragm is positioned right below the diaphragm pressing portion.

9. The multi-audio stethoscope head of claim 6, wherein, a portion of contact between the sound enhancing ring and the vibrating diaphragm is positioned between a sidewall of the through hole of the fastener and a radially inner face of the fastener sidewall.

10. The multi-audio stethoscope head of claim 6, wherein, the lower surface of the vibrating diaphragm between the sound enhancing ring and a radially inner face of the fastener sidewall is spaced from the upper surface of the head body at a radially outer side of the sound enhancing ring.

11. The multi-audio stethoscope head of claim 6, wherein, a gap is present between the lower surface of the vibrating diaphragm at a radially outer side of the sound enhancing ring and the upper surface of the head body, or a gap is present between the upper surface of the vibrating diaphragm at a radially outer side of the sound enhancing ring and the diaphragm pressing portion of the fastener.

12. The multi-audio stethoscope head of claim 6, wherein, an annular groove is provided in the upper surface of the head body, and the sound enhancing ring is placed in the annular groove, with at least a part of the sound enhancing ring extending out of the annular groove.

13. The multi-audio stethoscope head of claim 6, wherein, the vibrating diaphragm is a flat sheet made by a single material that has a uniform thickness.

14. The multi-audio stethoscope head of claim 6, wherein, an edge of the vibrating diaphragm is free of elastic coating.

15. The multi-audio stethoscope head of claim 1, wherein a distance from the protruding pole to the center of the sound guiding hole is no more than 50% of a radius of the sound collecting cavity.

* * * * *